US010351447B2

(12) United States Patent
Yamaguchi et al.

(10) Patent No.: US 10,351,447 B2
(45) Date of Patent: Jul. 16, 2019

(54) WATER TREATMENT SYSTEM (71) Applicant: METAWATER CO., LTD., Tokyo (JP)

(72) Inventors: Yuka Yamaguchi, Tokyo (JP); Yusuke Hisamoto, Tokyo (JP); Hiroshi Munehira, Tokyo (JP); Shigeyuki Okada, Tokyo (JP); Dabide Yamaguchi, Tokyo (JP)

(73) Assignee: Metawater Co., Ltd., Chiyoda-Ku (JP)

( * ) Notice: Subject to any disclaimer, the term of this patent is extended or adjusted under 35 U.S.C. 154(b) by 301 days.

(21) Appl. No.: 15/216,901

(22) Filed: Jul. 22, 2016

(65) Prior Publication Data

US 2016/0326030 A1 Nov. 10, 2016

Related U.S. Application Data (63) Continuation of application No. PCT/JP2014/006120, filed on Dec. 8, 2014.

(30) Foreign Application Priority Data

Mar. 31, 2014 (JP) ................................ 2014-072777

(51) Int. Cl.
*C02F 1/52* (2006.01)
*B01D 21/30* (2006.01)
(Continued)

(52) U.S. Cl.
CPC ............ *C02F 1/5209* (2013.01); *B01D 21/01* (2013.01); *B01D 21/08* (2013.01); *B01D 21/30* (2013.01);
(Continued)

(58) Field of Classification Search
None
See application file for complete search history.

(56) References Cited

U.S. PATENT DOCUMENTS

| 8,303,893 | B2 | 11/2012 | Yamaguchi et al. |
| 2011/0266227 | A1* | 11/2011 | Yamaguchi ........... C02F 1/5209 210/709 |
| 2012/0111117 | A1* | 5/2012 | Prakash ............... G01N 29/032 73/599 |

FOREIGN PATENT DOCUMENTS

| JP | 62-250919 A1 | 10/1987 |
| JP | 06-31291 A1 | 2/1994 |

(Continued)

OTHER PUBLICATIONS

International Search Report and Written Opinion (Application No. PCT/JP2014/006120) dated Jan. 27, 2015.

(Continued)

*Primary Examiner* — Richard C Gurtowski
(74) *Attorney, Agent, or Firm* — Burr & Brown, PLLC (57) ABSTRACT Provided is a water treatment system that prevents overlook and misdetection of abnormal flocculation. The water treatment system includes a mix tank, a flocculation tank, a plurality of floc-particle-diameter measurement devices, a fault detection device that detects abnormal flocculation, and a notification device that notifies occurrence of the abnormal flocculation. The fault detection device includes: a calculator that calculates at least one of a difference and a ratio between particle diameters of floc; a storage that stores therein a tolerable range of at least one of the difference and the ratio between the particle diameters of floc; a determiner that, when the calculated value is within the tolerable range, determines that it is normal, and when the calculated value is outside the tolerable range, determines that it is abnormal; and an outputter that transmits an abnormal flocculation detection signal to the notification device.

17 Claims, 3 Drawing Sheets

(51) Int. Cl.
  *B01D 21/01*     (2006.01)
  *G01N 15/02*     (2006.01)
  *B01D 21/08*     (2006.01)
  *G01N 15/00*         (2006.01)

(52) U.S. Cl.
  CPC ........ *G01N 15/02* (2013.01); *C02F 2209/001* (2013.01); *C02F 2209/003* (2013.01); *C02F 2209/006* (2013.01); *C02F 2209/105* (2013.01); *G01N 2015/0092* (2013.01)

(56) References Cited

FOREIGN PATENT DOCUMENTS

| | | |
|---|---|---|
| JP | 06-277406 A1 | 10/1994 |
| JP | 07-112103 A1 | 5/1995 |
| JP | 07-204412 A1 | 8/1995 |
| JP | 10-202013 A1 | 8/1998 |
| JP | 2002-253905 A1 | 9/2002 |
| JP | 2011-253386 A1 | 12/2011 |
| KR | 10-2004-0079665 A1 | 9/2004 |

OTHER PUBLICATIONS

Extended European Search Report (Application No. 14888298.8) dated Oct. 9, 2017.

\* cited by examiner

WATER TREATMENT SYSTEM

BACKGROUND OF THE INVENTION

Field of the Invention

The present disclosure relates to a water treatment system, especially to a water treatment system that detects occurrence of a fault in flocculation using a coagulant.

Description of Related Art

Conventionally, a coagulation-sedimentation method is employed in various fields of water treatment, including purification of water, sewage treatment, industrial water treatment, and industrial wastewater treatment, as a way to remove suspended matters that are present in water to be treated.

Such a coagulation-sedimentation method coagulates suspended matters that are present in water to be treated, sediments the resultant floc (i.e., clumps), and thus, removes the suspended matters from the water to be treated. Accordingly, favorable progress of flocculation using a coagulant is requisite for any water treatment technology employing the coagulation-sedimentation method.

Hence, as one water treatment system employing the coagulation-sedimentation method, a water treatment system that allows favorable flocculation by regulating a dosage of the coagulant has been proposed (refer to, for example, Patent Literatures 1 and 2).

In detail, Patent Literature 1 proposes a water treatment system including a floc image detection device that is disposed in the vicinity of an intake of a flocculation reservoir and that captures an image of the coagulated floc. By regulating a dosage of the coagulant based on the characteristics of the condition of flocculation grasped by data detected by the floc image detection device, the system proposed in Patent Literature 1 detects abnormal flocculation due to excess or deficiency in the dosage of the coagulant within a short period of time and corrects the dosage of the coagulant quickly.

Patent Literature 2 proposes a water treatment system that provides good-quality treated water even when the water quality of water to be treated is abruptly changed, by mixing raw water with a coagulant in an agitation tank, while measuring a particle diameter of floc and an ultra-violet absorbance of dissolved organic matters in the agitation tank at the same time, and by regulating a dosing rate of the coagulant to obtain a predetermined or larger particle diameter of floc and a predetermined or smaller ultra-violet absorbance of the dissolved organic matters.

CITATION LIST

Patent Literatures

PTL 1: JPH06277406A
PTL 2: JPH07204412A

SUMMARY OF THE INVENTION

Technical Problems

In connection with the above, a water treatment system employing the coagulation-coagulation method for continuous treatment of water to be treated typically mixes the water to be treated with a coagulant in a mix tank to obtain coagulant-mixed water, and subsequently, gradually grows floc present in the coagulant-mixed water in a flocculation tank. However, in the aforementioned conventional technologies, the conditions of flocculation and the particle diameter of floc are measured only at a single location located on an upstream side (closer to the mix tank) in the water treatment system used for continuous treatment of water to be treated, and the detection of abnormal flocculation and the regulation of the dosage of the coagulant rely on the comparison between the measured forming condition and particle diameter and a predetermined desirable forming condition and particle diameter.

Accordingly, the aforementioned conventional technologies pose the problem that abnormal flocculation (e.g., abnormal flocculation caused by a failure of an agitation device disposed on a downstream side) occurring on the downstream side of the location at which the conditions of flocculation and the particle diameter of floc are measured cannot be detected.

Furthermore, according to the aforementioned conventional technologies in which occurrence of abnormal flocculation is determined based on the floc information measured at a single location in the water treatment system, it is impossible to determine whether or not floc is growing appropriately. That is to say, floc growth is affected by various factors, such as an agitation intensity in the flocculation tank, and the aforementioned conventional technologies have sometimes given rise to cases where it is determined that abnormal flocculation is occurring because floc growth has not reached a predetermined level at the location of measurement despite the fact that floc is growing appropriately in the water treatment system as a whole or cases where it is determined that abnormal flocculation is not occurring because floc growth has reached a predetermined level at the location of measurement despite the fact that floc is not growing appropriately in the water treatment system as a whole.

In view of the above, the present disclosure is to provide a water treatment system that prevents overlook and misdetection of abnormal flocculation.

Solution to Problems

One of aspects of the present disclosure, for solving the above problems advantageously, resides in a water treatment system, including: a mix tank in which water to be treated and a coagulant are mixed to obtain coagulant-mixed water; a flocculation tank in which floc present in the coagulant-mixed water is grown; a plurality of floc-particle-diameter measurement devices that are disposed at least one of the mix tank and the flocculation tank and that measure particle diameters of floc in different locations along a flow direction of the coagulant-mixed water; a fault detection device that detects abnormal floc formation by using the particle diameters of floc measured by the plurality of floc-particle-diameter measurement devices; and a notification device that notifies occurrence of the abnormal floc formation detected by the fault detection device, wherein the fault detection device includes: a calculator that calculates at least one of a difference and a ratio between particle diameters of floc measured by the plurality of the floc-particle-diameter measurement devices; a storage that stores therein a tolerable range of the at least one of the difference and the ratio between the particle diameters of floc; a determiner that compares a value calculated by the calculator with the tolerable range stored in the storage and that, when the calculated value is within the tolerable range, determines that normal flocculation is occurring, and when the calculated value is outside the tolerable range, determines that abnormal flocculation is occurring; and an outputter that transmits an abnormal flocculation detection signal to the notification device when the determiner determines that abnormal flocculation is occurring.

By thus using the plurality of floc-particle-diameter measurement devices and by determining occurrence of abnormal flocculation by using the difference and/or the ratio between the particle diameters of floc measured in the different locations along the flow direction of the coagulant-mixed water, overlook and misdetection of abnormal flocculation are prevented compared with cases where occurrence of abnormal flocculation is determined based on the floc information measured only at a single location.

In a preferred embodiment of the water treatment system according to the present disclosure, the calculator calculates the ratio between the particle diameters of floc, and the storage stores therein the tolerable range of the ratio between the particle diameters of floc. By determining occurrence of abnormal flocculation by using the ratio between the particle diameters of floc, the degree of floc growth between the locations at which the particle diameters are measured is grasped appropriately for determination of occurrence of abnormal flocculation.

In another preferred embodiment of the water treatment system according to the present disclosure, the water treatment system further includes: a water quality measurement device that measures water quality of at least one of the water to be treated and the coagulant-mixed water, wherein the storage stores therein a plurality of tolerable ranges in correspondence with the water qualities measurable by the water quality measurement device, and the determiner compares one of the plurality of tolerable ranges that corresponds to the water quantity measured by the water quality measurement device with the value calculated by the calculator. A tolerable range of the difference and the ratio between the particle diameters of floc is affected by a change in water quality of the water to be treated, and, by determining occurrence of abnormal flocculation by using one of the plurality of tolerable ranges that corresponds to the water quantity measured by the water quality measurement device, overlook and misdetection of abnormal flocculation are further prevented.

In yet another preferred embodiment of the water treatment system according to the present disclosure, the water treatment system further includes: a sedimentation tank in which floc grown in the flocculation tank is sedimented; and a treated water quality measurement device that measures water quality of treated water obtained as a result of the sedimentation of floc in the sedimentation tank, wherein the fault detection device further includes a corrector that corrects the tolerable range stored in the storage based on the water quality of the treated water measured by the treated water quality measurement device, and the corrector corrects the tolerable range as needed so that it is to be determined that abnormal flocculation is occurring when treated water within a predetermined water quality range is not obtained and that it is to be determined that abnormal flocculation is not occurring when treated water within the predetermined water quality range is obtained. Measuring the water quality of the treated water and correcting the tolerable range will allow the use of a tolerable range suited to an actual operational condition, and this further prevents overlook and misdetection of abnormal flocculation.

The phrase "corrects the tolerable range as needed" herein means that the corrector does not correct the tolerable range when the tolerable range stored in the storage is appropriate and does not need any correction.

In yet another preferred embodiment of the water treatment system according to the present disclosure, the water treatment system further includes: a water quality measurement device that measures water quality of at least one of the water to be treated and the coagulant-mixed water, wherein the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and the outputter also transmits an abnormal flocculation detection signal to the notification device when the particle diameter determiner determines that abnormal flocculation is occurring. Disposing the particle diameter determiner, which also determines occurrence of abnormal flocculation, allows detection of abnormal flocculation that would not be detected simply by using the ratio and the difference of the particle diameters of floc, and this even further prevents overlook and misdetection of abnormal flocculation.

Advantageous Effect

The water treatment system according to the present disclosure prevents overlook and misdetection of abnormal flocculation.

DETAILED DESCRIPTION OF THE INVENTION

Embodiments of the present disclosure will be described below with reference to the drawings.

A water treatment system according to the present disclosure may be used to treat raw water (water to be treated) taken from rivers or the like in, for example, a water purifying plant. Note that, however, water to be treated by a water treatment system according to the present disclosure is not limited to river water or the like.

Figure 1:
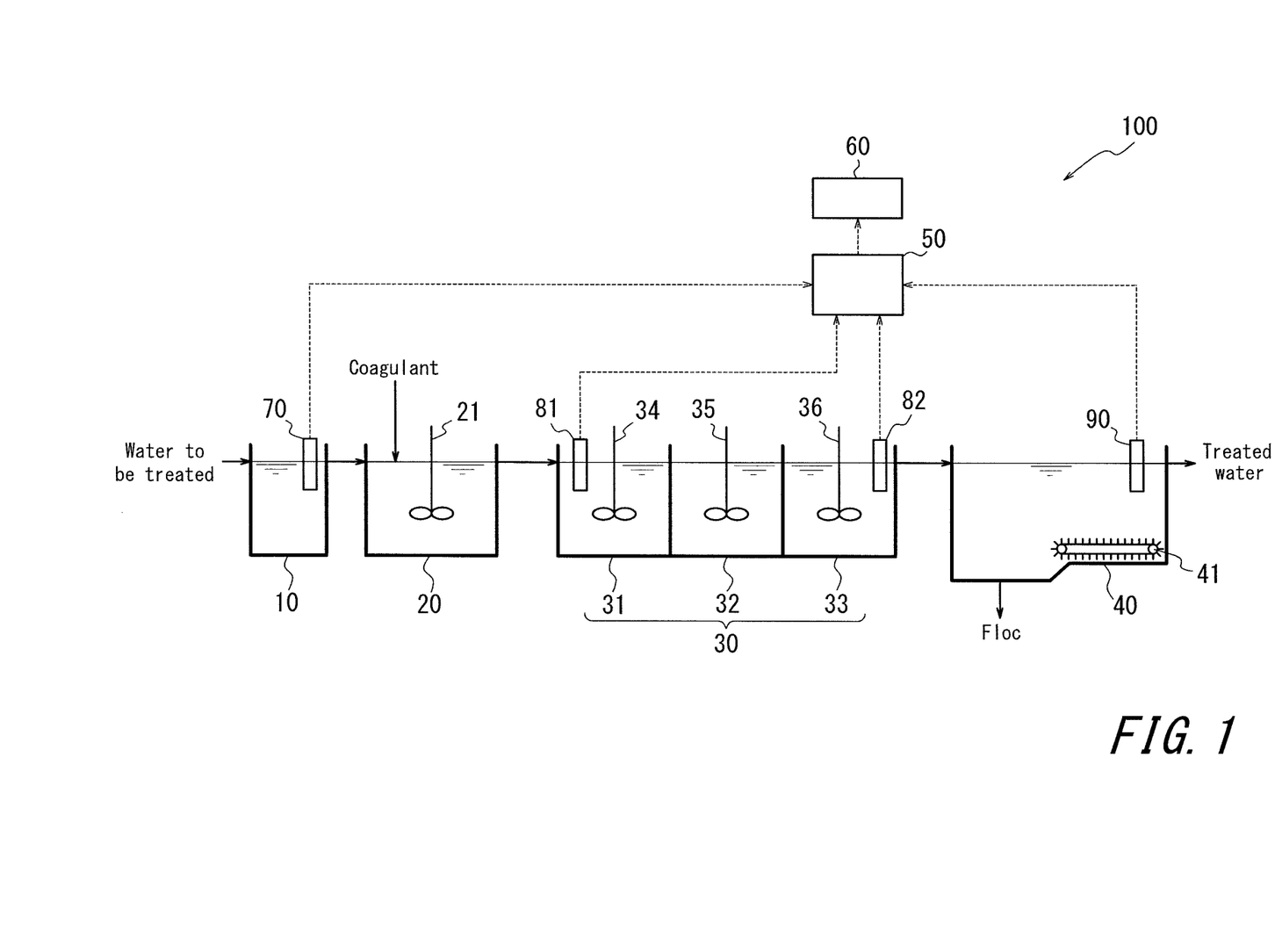
FIG. 1 illustrates a schematic configuration of a typical water treatment system according to the present disclosure.

Here, FIG. 1 illustrates an example of the schematic configuration of a water treatment system according to the present disclosure. A water treatment system 100 of FIG. 1 includes a tank (hereinafter, called the to-be-treated water tank) 10 for water to be treated, a mix tank 20, a flocculation tank 30 whose inside is divided into three flocculation compartments 31, 32, and 33, and a sedimentation tank 40. In the water treatment system 100, water to be treated, supplied from the to-be-treated water tank 10, and a coagulant are mixed in the mix tank 20 by using an agitator 21.

Coagulant-mixed water, which is obtained as a result of mixing the water to be treated and the coagulant in the mix tank 20, is supplied to the flocculation tank 30 to be flown through the first flocculation compartment 31, the second flocculation compartment 32, and the third flocculation compartment 33 in the flocculation tank 30 sequentially. In the flocculation tank 30, floc present in the coagulant-mixed water grow under agitation using agitators 34, 35, and 36 disposed respectively in the flocculation compartments 31, 32, and 33. After flowing out of the flocculation tank 30, floc present in the coagulant-mixed water is sedimented in the sedimentation tank 40. Furthermore, treated water, which is obtained as a result of sedimenting floc grown in the flocculation tank 30 in the sedimentation tank 40, may be optionally supplied to a filtration tank (which is not illustrated) for further treatment. Floc sedimenting in the sedimentation tank 40 is scraped by using a scraper 41 disposed in the bottom of the sedimentation tank 40 and subsequently discharged outside the sedimentation tank 40 for treatment.

Additionally, in the water treatment system 100, the dosing rate of the coagulant, as well as the magnitude of agitation intensity in the mix tank 20 and the flocculation tank 30, is not limited to a particular rate (magnitude) and may be determined by a known technique. For example, dosing rates of the coagulant and magnitudes of agitation intensity may be set in advance in correspondence with water qualities of the water to be treated, and the dosing rate of the coagulant and the magnitude of agitation intensity may be regulated to the rate and the magnitude corresponding to the measured water quality of the water to be treated.

Furthermore, as a mechanism to detect occurrence of a fault in flocculation using a coagulant and to notify outside of the occurrence of a fault detected, the water treatment system 100 includes a fault detection device 50 that detects abnormal floc formation and also includes a notification device 60 that notifies the outside of occurrence of the abnormal floc formation detected by the fault detection device 50.

Moreover, as a mechanism to provide information required for the detection of abnormal floc formation to the fault detection device 50, the water treatment system 100 includes a device (hereinafter, called the to-be-treated water quality measurement device) 70 that measures the water quality of the water to be treated, a first floc-particle-diameter measurement device 81 and a second floc-particle-diameter measurement device 82 that measure the particle diameters of floc present in the flocculation tank 30, and a treated water quality measurement device 90 that measures the water quality of the treated water in the sedimentation tank 40.

Figure 2:
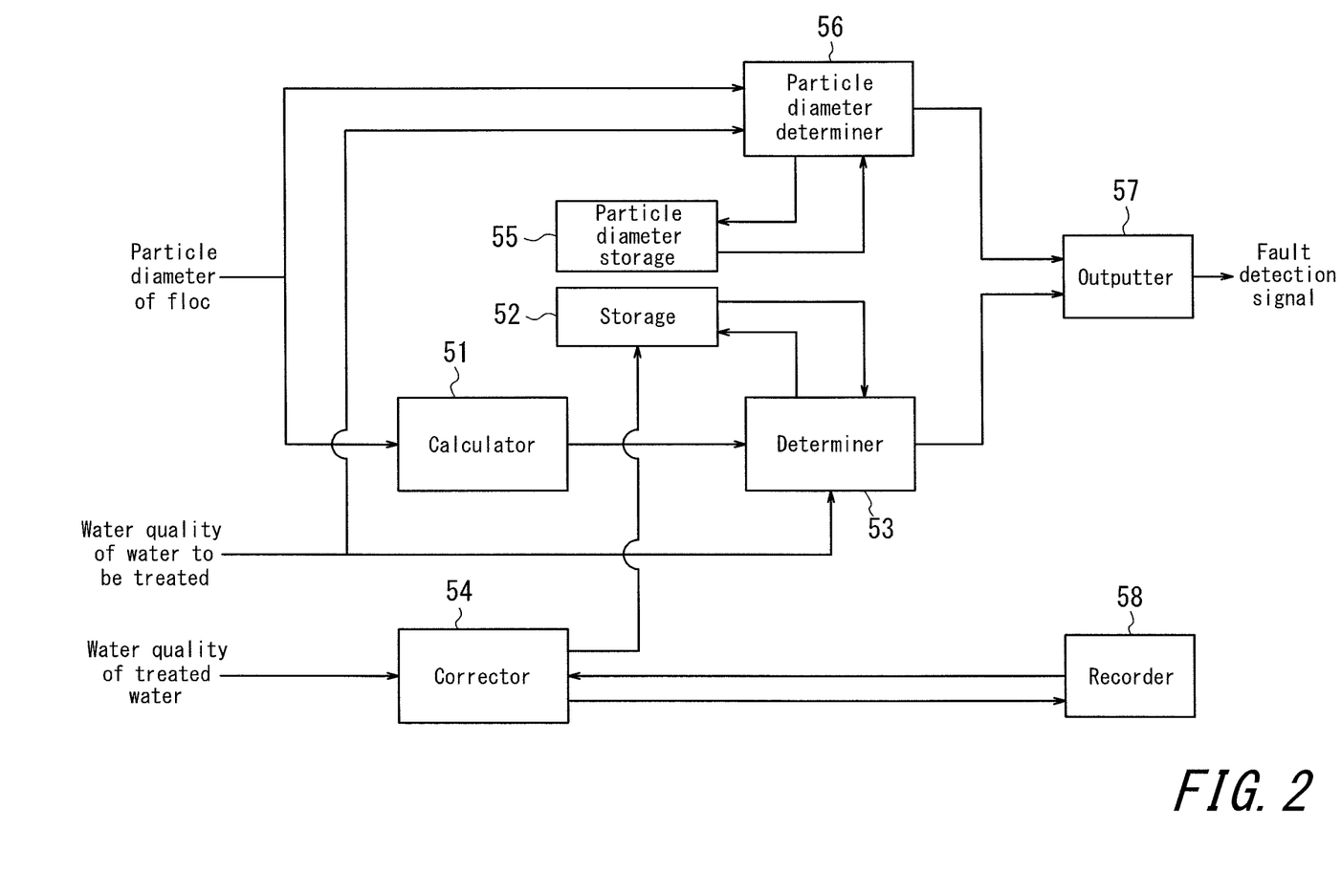
FIG. 2 illustrates a schematic configuration of a fault detection device included in a water treatment system of FIG. 1.

Herein, the fault detection device 50 included in the water treatment system 100 is a device that detects abnormal flocculation by using at least particle diameters of floc (hereinafter, simply referred as "particle diameters of floc") that are measured by a first floc-particle-diameter measurement device 81 and a second floc-particle-diameter measurement device 82. The fault detection device 50 is configured by using a known processing device, such as a computer. As illustrated in FIG. 2, the fault detection device 50 includes a calculator 51, a storage 52, a determiner 53, a corrector 54, a particle diameter storage 55, a particle diameter determiner 56, an outputter 57, and a recorder.

In the fault detection device 50, the calculator 51 calculates a difference and/or a ratio between a first particle diameter of floc measured by the first floc-particle-diameter measurement device 81 and a second particle diameter of floc measured by the second floc-particle-diameter measurement device 82. Then, the calculated value (a difference and/or a ratio) that the calculator 51 calculates is transmitted to the determiner 53.

The storage 52 stores therein a tolerable range of the value calculated by the calculator 51. In detail, the storage 52 stores therein a plurality of tolerable ranges of the calculated value, in correspondence with water qualities (e.g., the levels of turbidity, pH, water temperature, color, alkalinity, and concentrations of coagulation-preventing substances) of the water to be treated that are measurable by the to-be-treated water quality measurement device 70.

The tolerable ranges of the calculated value that are stored in the storage 52 may be set, for example, by conducting coagulation tests on water to be treated having different water qualities in advance and by obtaining a range of values that the difference and/or the ratio between the first particle diameter of floc and the second particle diameter of floc may take when flocculation is in favorable progress. Tolerable ranges of the calculated value may be brought into correspondence with water qualities of the water to be treated in any way without limitation. In detail, when, for example, the level of turbidity is used to indicate the water quality of the water to be treated, tolerable ranges of the calculated value may be set individually for all turbidity levels that the water to be treated may take, or, a different tolerable range of the calculated value may be set for each of predetermined ranges of turbidity level in a graded manner. Alternatively, a combination of, for example, two or more types of water quality may be brought into correspondence with each tolerable range of the calculated value.

Additionally, when the dosing rate of the coagulant and the magnitude of agitation intensity are regulated to a rate and a magnitude that are set in advance in accordance with the water quality of water to be treated as described above in the water treatment system 100, the aforementioned coagulation tests are preferably conducted in consideration of dosing rates of the coagulant and agitation intensities corresponding to the water qualities of the water to be treated.

The determiner 53 compares the calculated value calculated by the calculator 51 with the corresponding tolerable range stored in the storage 52, and, when the calculated value is within the tolerable range, determines that normal flocculation is occurring, and when the calculated value is outside the tolerable range, determines that abnormal flocculation is occurring. In more detail, based on the water quality of the water to be treated as measured by the to-be-treated water quality measurement device 70, the determiner 53 firstly acquires, from the storage 52, one of the tolerable ranges of the calculated value that corresponds to the water quality (e.g., the turbidity level) of the water to be treated. Subsequently, the determiner 53 compares the tolerable range of the calculated value acquired from the storage 52, with the calculated value calculated by the calculator 51, to determine whether the calculated value is within the tolerable range. Then, when the calculated value is within the tolerable range, the determiner 53 determines that normal flocculation is occurring, and when the calculated value is outside the tolerable range, the determiner 53 determines that abnormal flocculation is occurring, and the determiner 53 transmits a result of the determination to the outputter 57.

Figure 3:
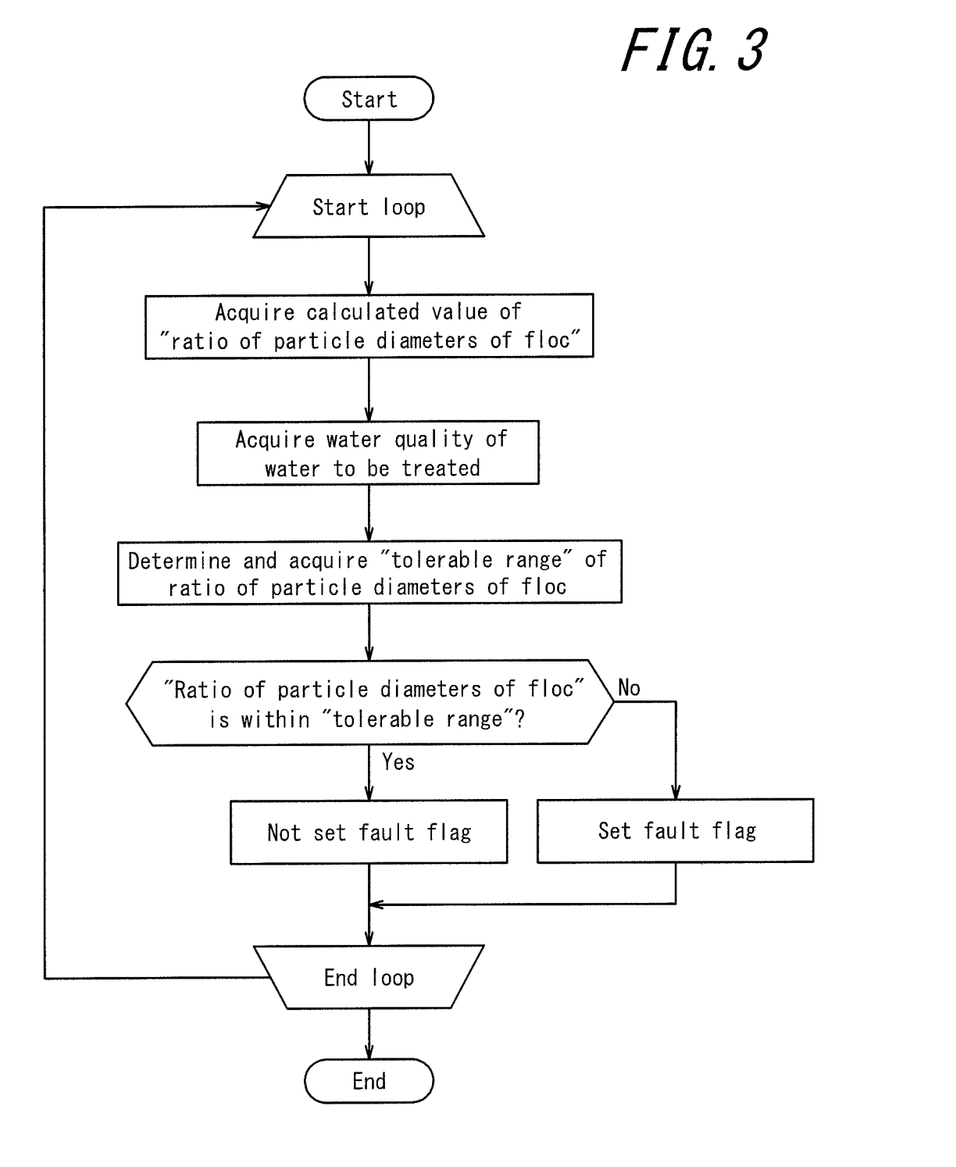
FIG. 3 is a flowchart illustrating exemplary operation details of a determiner included in a fault detection device of FIG. 2.

In more detail, as FIG. 3 illustrates an exemplary operation flow of the determiner 53 when, for example, the ratio between the first particle diameter of floc and the second particle diameter of floc is used as a calculated value, once detection of abnormal flocculation by the fault detection device 50 is started, the determiner 53 repeats the following operations. That is to say, the determiner 53 firstly acquires, from the calculator 51, a calculated value of the ratio between the particle diameters of floc. The determiner 53 also acquires, from the to-be-treated water quality measurement device 70 or from the recorder 58 which is later described, the water quality of the water to be treated measured by the to-be-treated water quality measurement device 70. Subsequently, the determiner 53 accesses the storage 52 to select, determine, and acquire the tolerable range of the ratio between the particle diameters of floc that corresponds to the water quality of the water to be treated. Then, the determiner 53 compares the tolerable range of the ratio between the particle diameters of floc acquired from the storage 52, with the ratio between the particle diameters of floc calculated by the calculator 51, to determine whether the calculated ratio between the particle diameters of floc is within the acquired tolerable range. When the ratio between the particle diameters of floc is within the tolerable range, the determiner 53 determines that normal flocculation is occurring (and does not set a fault flag), and when the ratio between the particle diameters of floc is outside the tolerable range, the determiner 53 determines that abnormal flocculation is occurring (and set a fault flag), and the determiner 53 transmits a result of the determination to the outputter 57.

Based on the water quality (e.g., the levels of turbidity, pH, color, and alkalinity) of the treated water measured by the treated water quality measurement device 90, the corrector 54 corrects the corresponding tolerable range of the calculated value stored in the storage 52 to an appropriate range as needed. In detail, taking residence time of the coagulant-mixed water into consideration, the corrector 54 firstly acquires, from the recorder 58 which is later described, a result of the determination made by the determiner 53 about the treated water, the water quality of which is measured by the treated water quality measurement device 90, and the calculated value and the tolerable range of the calculated value used by the determiner 53 for making the determination. Secondly, by using the result of the determination made by the determiner 53 and acquired from the recorder 58, the water quality of the treated water measured by the treated water quality measurement device 90, and a predetermined water quality range set in advance, the corrector 54 determines whether or not the result of the determination (about whether or not abnormal flocculation is occurring) made by the determiner 53 in the past about the treated water, the water quality of which is measured by the treated water quality measurement device 90, has been appropriate. That is to say, the corrector 54 determines that the result of the determination made by the determiner 53 has been appropriate when the following condition (1) or (2) applies and determines that the result of the determination made by the determiner 53 has been inappropriate when the following condition (3) or (4) applies. When determining that the result of the determination made by the determiner 53 has been appropriate, the corrector 54 does not correct anything or corrects the tolerable range of the calculated value stored in the storage 52 to the extent that the correction does not affect appropriateness of the result of the determination made by the determiner 53. On the other hand, when determining that the result of the determination made by the determiner 53 has been inappropriate, the corrector 54 corrects the tolerable range stored in the storage 52 to a tolerable range with which the result of the determination made by the determiner 53 would have been appropriate. In more detail, at least when the result of the determination made by the determiner 53 has been inappropriate, the corrector 54 obtains, based on the calculated value and the tolerable range of the calculated value used by the determiner 53 for making the determination, a tolerable range of the calculated values with which the result of the determination made by the determiner 53 would have been appropriate and corrects the tolerable range stored in the storage 52 to the obtained tolerable range. Optionally, even when the result of the determination made by the determiner 53 has been appropriate, the corrector 54 may also correct the tolerable range stored in the storage 52 as needed.

(1) The determiner 53 determines that abnormal flocculation is not occurring, and the measured water quality of the treated water is within the predetermined water quality range.

(2) The determiner 53 determines that abnormal flocculation is occurring, and the measured water quality of the treated water is outside the predetermined water quality range.

(3) Although the determiner 53 determines that abnormal flocculation is not occurring, the measured water quality of the treated water is outside the predetermined water quality range.

(4) Although the determiner 53 determines that abnormal flocculation is occurring, the measured water quality of the treated water is within the predetermined water quality range.

Additionally, the "predetermined water quality range" of the treated water may be determined in accordance with a required water quality of the treated water. When the result of the determination made by the determiner 53 has been appropriate, the correction may be made to the tolerable range of the calculated value for the purpose of, for example, improving accuracy in detecting abnormal flocculation. In detail, for example, when, although the result of the determination made by the determiner 53 has been appropriate, the measured water quality of the treated water is close to the upper limit or the lower limit of the predetermined water quality range, the corrector 54 may narrow or shift the tolerable range of the calculated value. By doing so, the corrector 54 allows detection of a minor fault in flocculation that cannot be detected based on the previous tolerable range of the calculated value, and accordingly, the water treatment system 100 is able to detect abnormal flocculation with even higher precision. Additionally, the degree to which the tolerable range is narrowed or shifted by the corrector 54 correcting the tolerable range may be determined by any methods, such as reference to various data stored in the later-described recorder 58 and tests conducted in advance.

The particle diameter storage 55 stores therein a tolerable particle diameter range of the first particle diameter of floc and/or the second particle diameter of floc. In detail, the particle diameter storage 55 stores therein a plurality of tolerable particle diameter ranges of the first particle diameter of floc and/or the second particle diameter of floc, in correspondence with water qualities (e.g., the levels of turbidity, pH, water temperature, color, alkalinity, and concentrations of a coagulation-preventing substances) of the water to be treated that are measurable by the to-be-treated water quality measurement device 70.

The tolerable particle diameter ranges of the first particle diameter of floc and/or the second particle diameter of floc that are stored in the particle diameter storage 55 may be set, for example, by conducting coagulation tests on water to be treated having different water qualities in advance and by obtaining a range of values that of the first particle diameter of floc and/or the second particle diameter of floc may take when flocculation is in favorable progress. Tolerable particle diameter ranges of the first particle diameter of floc and/or the second particle diameter of floc may be brought into correspondence with water qualities of the water to be treated in any way without limitation. In detail, when, for example, the level of turbidity is used to indicate the water quality of the water to be treated, tolerable particle diameter ranges of the first particle diameter of floc and/or the second particle diameter of floc may be set individually for all turbidity levels that the water to be treated may take, or, different particle diameter ranges of the first particle diameter of floc and/or the second particle diameter of floc may be set for predetermined ranges of turbidity level in a graded manner. Alternatively, a combination of, for example, two or more types of water quality may be brought into correspondence with each tolerable particle diameter range of the first particle diameter of floc and/or the second particle diameter of floc.

Additionally, when the dosing rate of the coagulant and the magnitude of agitation intensity are regulated to a rate and a magnitude that are set in advance in accordance with the water quality of the water to be treated as described above in the water treatment system 100, the aforementioned coagulation tests are preferably conducted in consideration of dosing rates of the coagulant and agitation intensities corresponding to the water qualities of the water to be treated, similarly to the tolerable ranges of the calculated value stored in the storage 52.

The particle diameter determiner 56 compares the first particle diameter of floc and/or the second particle diameter of floc, with the corresponding tolerable particle diameter range(s) stored in the particle diameter storage 55, and, when the first particle diameter of floc and/or the second particle diameter of floc are/is within the tolerable particle diameter range(s), determines that normal flocculation is occurring, and when the first particle diameter of floc and/or the second particle diameter of floc are/is outside the tolerable range(s), determines that abnormal flocculation is occurring. In more detail, based on the water quality of the water to be treated as measured by the to-be-treated water quality measurement device 70, the particle diameter determiner 56 firstly acquires, from the particle diameter storage 55, one of the tolerable particle diameter ranges of the first particle diameter of floc and/or the second particle diameter of floc that correspond(s) to the water quality (e.g., the turbidity level) of the water to be treated. Subsequently, the particle diameter determiner 56 compares the tolerable particle diameter range of the first particle diameter of floc and/or the second particle diameter of floc acquired from the particle diameter storage 55, with the first particle diameter of floc and/or the second particle diameter of floc, to determine whether the first particle diameter of floc and/or the second particle diameter of floc are/is within the tolerable range(s). Then, when the first particle diameter of floc and/or the second particle diameter of floc are/is within the tolerable particle diameter range(s), the particle diameter determiner 56 determines that normal flocculation is occurring, and when the first particle diameter of floc and/or the second particle diameter of floc are/is outside the tolerable particle diameter range(s), the particle diameter determiner 56 determines that abnormal flocculation is occurring, and the particle diameter determiner 56 transmits a result of the determination to the outputter 57.

The outputter 57 transmits an abnormal flocculation detection signal to the notification device 60 when at least one of the determiner 53 and the particle diameter determiner 56 has determined that abnormal flocculation is occurring. When both the determiner 53 and the particle diameter determiner 56 have determined that normal flocculation is occurring, the outputter 57 either transmits a normal flocculation signal to the notification device 60 or does not transmit any signal.

The storage 58 stores therein data (e.g., the water quality of water to be treated, particle diameter of floc, and the water quality of treated water) that the fault detection device 50 receives from the outside, results of the determination made by the determiner 53, the calculated values and the tolerable ranges of the calculated values used by the determiner 53 for making the determination, results of the determination made by the particle diameter determiner 56, and the particle diameters of floc and the tolerable particle diameter ranges used by the particle diameter determiner 56 for making the determination, in relations with each other. In detail, the recorder 58 stores the aforementioned information in relations with, for example, operating time of the water treatment system 100. Herein, a time period for which the recorder 58 stores and holds the information may be set suitably in accordance with purposes of the information.

Furthermore, the notification device 60 included in the water treatment system 100 is a device that notifies occurrence of abnormal flocculation upon receiving an abnormal flocculation detection signal from the outputter 57 of the fault detection device 50. The notification device 60 may be a display device or an alert device that notifies a human being (e.g., a monitor) of occurrence of abnormal flocculation or may be a communication device that notifies a control device (e.g., a control device for a dosage of the coagulant) included in the water treatment system 100 of occurrence of abnormal flocculation.

Moreover, the to-be-treated water quality measurement device 70 is a device that measures the water quality (e.g., the levels of turbidity, pH, water temperature, color, alkalinity, and concentrations of coagulation-preventing substances) of the water to be treated that is used in the fault detection device 50. Additionally, a known sensor may be employed as the to-be-treated water quality measurement device 70.

Moreover, the first floc-particle-diameter measurement device 81 and the second floc-particle-diameter measurement device 82 are devices that are disposed in different locations along the flow direction of the coagulant-mixed water and that measure the particle diameter of floc present in the coagulant-mixed water. In detail, the first floc-particle-diameter measurement device 81 is disposed in the first flocculation compartment 31 and the second floc-particle-diameter measurement device 82 is disposed in the third flocculation compartment 33. Additionally, a known floc-particle-diameter sensor may be employed as the first floc-particle-diameter measurement device 81 and the second floc-particle-diameter measurement device 82.

Moreover, the treated water quality measurement device 90 is a device that measures the water quality (e.g., the levels of turbidity, pH, color, and alkalinity) of the treated water that is used in the fault detection device 50. Additionally, a known sensor may be employed as the treated water quality measurement device 90.

Thus, according to the water treatment system 100 with the above configuration, since the determiner 53 included in the fault detection device 50 determines whether or not abnormal flocculation is occurring by using the difference and/or the ratio between the first particle diameter of floc and the second particle diameter of floc, overlook and misdetection of abnormal flocculation are prevented. That is to say, if, for example, only the first particle diameter of floc is used to determine occurrence of abnormal flocculation, it is impossible to detect abnormal flocculation (e.g., abnormal flocculation caused by a failure of the agitation devices 35 and 36) occurring in the second flocculation compartment 32 and the third flocculation compartment 33 that are located on the downstream side of the first floc-particle-diameter measurement device 81. However, the water treatment system 100, which also uses the second particle diameter of floc, prevents such overlook of abnormal flocculation. Similarly, if, for example, only the first particle diameter of floc or the second particle diameter of floc is used to determine occurrence of abnormal flocculation, since the condition of floc growth cannot be grasped solely from a measurement value obtained at a single location, it is impossible for the water treatment system as a whole to determine whether or not floc is growing appropriately, and this might result in overlook and misdetection of abnormal flocculation when, for example, the measurement value falls within the corresponding tolerable range by chance. However, the water treatment system 100, which determines whether or not abnormal flocculation is occurring by using the difference and/or the ratio between the first particle diameter of floc and the second particle diameter of floc, prevents such overlook and misdetection of abnormal flocculation.

Additionally, the fault detection device 50 included in the water treatment system 100 preferably uses at least the ratio between the first particle diameter of floc and the second particle diameter of floc and more preferably, uses only the ratio between the first particle diameter of floc and the second particle diameter of floc, although both of the difference between the first particle diameter of floc and the second particle diameter of floc and the ratio between the first particle diameter of floc and the second particle diameter of floc may be used. That is to say, in the fault detection device 50 included in the water treatment system 100, preferably, the calculator 51 calculates the ratio between the first particle diameter of floc and the second particle diameter of floc, the storage 52 stores the tolerable range of the ratio between the first particle diameter of floc and the second particle diameter of floc, and the determiner 53 determines whether or not abnormal flocculation is occurring by using the ratio between the first particle diameter of floc and the second particle diameter of floc.

The reason is that, by determining occurrence of abnormal flocculation by using the ratio between the first particle diameter of floc and the second particle diameter of floc, the degree of floc growth between the locations at which the particle diameters are measured is grasped even more appropriately for determination of occurrence of abnormal flocculation. In detail, providing that the difference between the first particle diameter of floc and the second particle diameter of floc is used in two cases (e.g., a case where the first particle diameter of floc is 10 μm and the second particle diameter of floc is 20 μm, and a case where the first particle diameter of floc is 1 μm and the second particle diameter of floc is 11 μm) where the floc growth rates are completely different, the same difference might be obtained in both the cases, and this might make it difficult to grasp the degree of floc growth appropriately to determine occurrence of abnormal flocculation. However, by using the ratio, the degree of floc growth is grasped appropriately to determine occurrence of abnormal flocculation. Furthermore, compared with the amount of the difference between the first particle diameter of floc and the second particle diameter of floc, the amount of ratio there between is less likely to be affected by a change in water quality of the water to be treated, a change in conditions of agitation in the flocculation tank 30, and so forth, and advance preparation of the tolerable range of the ratio to be stored in the storage 52 may be simplified. Besides, advance preparation of the tolerable ranges, for both the ratio between the first particle diameter of floc and the second particle diameter of floc and the difference between the first particle diameter of floc and the second particle diameter of floc, to be stored in the storage 52 is a complicated task.

Moreover, when the difference and/or the ratio between the first particle diameter of floc and the second particle diameter of floc are/is calculated by the calculator 51 of the fault detection device 50 included in the water treatment system 100, although the first particle diameter of floc and the second particle diameter of floc that are measured at the same time may be used, it is preferable to use the second particle diameter of floc and the first particle diameter of floc measured in the first floc-particle-diameter measurement device 81 when the coagulant-mixed water, for which the second particle diameter of floc is measured in the second floc-particle-diameter measurement device 82, passes the location of the first floc-particle-diameter measurement device 81. That is to say, the calculator 51 preferably acquires, from the recorder 58, the first particle diameter of floc measured when the coagulant-mixed water, for which the second particle diameter of floc is measured, passes the location of the first floc-particle-diameter measurement device 81 and calculates the calculated value by using the first particle diameter of floc and the second particle diameter of floc acquired from the recorder 58. The reason is that, by the calculator 51 calculating the calculated value by using the first particle diameter of floc measured when the coagulant-mixed water, for which the second particle diameter of floc is measured, passes the location of the first floc-particle-diameter measurement device 81, the condition of growth of the same subject (floc group) is grasped for determination of occurrence of abnormal flocculation with even higher precision, regardless of changes in water quality of the water to be treated, the conditions of coagulation, and so forth with the passage of time.

Moreover, according to the water treatment system 100 with the above configuration, the storage 52 stores therein the plurality of tolerable ranges of the calculated values, in correspondence with the water qualities of the water to be treated, and the determiner 53 determines occurrence of abnormal flocculation by using one of the plurality of the tolerable ranges that corresponds to the water quality of the water to be treated. Accordingly, even when the water quality of the water to be treated is changed, it is ensured that overlook and misdetection of abnormal flocculation may be prevented.

Moreover, according to the water treatment system 100 with the above configuration, since the corrector 54 corrects the tolerable ranges stored in the storage 52 in accordance with the water qualities of the treated water as needed, occurrence of abnormal flocculation is determined by using a tolerable range more suited to the actual operational condition of the water treatment system 100, compared with cases where tolerance ranges determined by, for example, tests conducted in advance are solely used. Consequently, overlook and misdetection of abnormal flocculation are further prevented.

Additionally, the correction by the corrector 54 may be made constantly or intermittently at every predetermined interval.

Moreover, according to the water treatment system 100 with the above configuration, since the particle diameter storage 55 and the particle diameter determiner 56, in addition to the calculator 51, the storage 52, and the determiner 53, are employed for determination of occurrence of abnormal flocculation, it is further ensured that overlook and misdetection of abnormal flocculation may be prevented. That is to say, only with the difference and/or the ratio between the first particle diameter of floc and the second particle diameter of floc, it is inevitably determined that abnormal flocculation is not occurring if the difference and/or the ratio between the particle diameters are/is just within the tolerable range(s), even when the particle diameters of floc have not reached a desired particle diameter. However, by determining occurrence of abnormal flocculation by using the particle diameter storage 55 and the particle diameter determiner 56 additionally, occurrence of abnormal flocculation is detected if the particle diameters of floc have not reached a desired particle diameter even when the difference and/or the ratio between the particle diameters are/is within the tolerable range(s). Accordingly, it is further ensured that overlook and misdetection of abnormal flocculation may be prevented.

Moreover, according to the water treatment system 100 with the above configuration, the particle diameter storage 55 stores therein the plurality of tolerable particle diameter ranges in correspondence with the water qualities of the water to be treated, and the particle diameter determiner 56 determines occurrence of abnormal flocculation by using one of the plurality of the tolerable particle diameter ranges that corresponds to the water quality of the water to be treated. Accordingly, even when the water quality of the water to be treated is changed, it is ensured that overlook and misdetection of abnormal flocculation may be prevented.

Herein, although the particle diameter determiner 56 may use at least one of the first particle diameter of floc and the second particle diameter of floc for the determination of occurrence of abnormal flocculation, it is preferable to use the second particle diameter of floc from the perspective of preventing overlook of abnormal flocculation, it is preferable to use the first particle diameter of floc from the perspective of detecting abnormal flocculation at an early stage, and it is more preferable to use both the particle diameters of floc. Using the second particle diameter of floc promotes prevention of overlook of abnormal flocculation compared with cases using only the first particle diameter of floc. On the other hand, using the first particle diameter of floc promotes early detection of occurrence of abnormal flocculation on the upstream side in the flow direction of the coagulant-mixed water compared with cases using only the second particle diameter of floc.

The water treatment system according to the present disclosure has been described with the aid of one example. However, the water treatment system according to the present disclosure is not limited to the example, and changes may be made to the water treatment system according to the present disclosure as appropriate.

For example, although the water treatment system 100 according to the example uses the water quality of the water to be treated that the to-be-treated water quality measurement device 70 measures, the water treatment system according to the present disclosure may also use the water quality (e.g., pH) of the coagulant-mixed water measured in the mix tank 20 or in the flocculation tank 30, in replacement of or in addition to the water quality of the water to be treated.

Furthermore, although the water treatment system 100 according to the example employs two floc-particle-diameter measurement devices 81 and 82, the water treatment system according to the present disclosure may also employ three or more floc-particle-diameter measurement devices. When three or more floc-particle-diameter measurement devices are employed, the calculator 51 may calculate a difference and/or a ratio between particle diameters of floc measured by any two of the three or more floc-particle-diameter measurement devices.

Moreover, although, in the water treatment system 100 according to the example, the floc-particle-diameter measurement devices 81 and 82 are respectively disposed in the first flocculation compartment 31 and the third flocculation compartment 33, the floc-particle-diameter measurement devices may also be disposed in any locations in the mix tank 20 and the flocculation tank 30. Additionally, when the flocculation tank includes a plurality of flocculation compartments, a floc-particle-diameter measurement device is preferably disposed at least in one of the plurality of flocculation compartments that is located on the most downstream side in the flocculation tank, from the perspective of preventing overlook of abnormal flocculation. Furthermore, from the perspective of detecting occurrence of abnormal flocculation at an early stage on the upstream side in the flow direction of the coagulant-mixed water, a floc-particle-diameter measurement device is preferably disposed in the mix tank or in one of the plurality of flocculation compartments that is located on the most upstream side in the flocculation tank.

Moreover, although, in the water treatment system 100 according to the example, the corrector 54 corrects a tolerable range of the calculated values stored in the storage 52, the corrector 54 may also correct a tolerable particle diameter range stored in the particle diameter storage 55 in a similar manner to the correction made to the tolerable range of the calculated values stored in the storage 52.

Moreover, in the water treatment system 100 according to the example, the storage 52 stores therein the plurality of tolerable ranges of the calculated values, in correspondence with the water qualities of the water to be treated, and the determiner 53 acquires, from the storage 52, one of the plurality of tolerable ranges that corresponds to the water quality of the water to be treated for determination of occurrence of abnormal flocculation. However, the storage 52 may also store therein only a single tolerable range of the calculated values regardless of the water quality of the water to be treated, or a plurality of tolerable ranges of the calculated values in correspondence with a factor other than the water quality. For example, the storage 52 may store therein a plurality of tolerable ranges of the calculated values, in correspondence with dosing rates of the coagulant in the mix tank 20 and/or agitation intensities in the mix tank 20 and the flocculation tank 30. Then, the determiner 53 may acquire, from the storage 52, one of the plurality of tolerable ranges of the calculated values that corresponds to the dosing rate of the coagulant and/or the agitation intensity that are/is detected by using a known technique, such as a flow meter and a revolution counter, for determination of occurrence of abnormal flocculation. By thus using the tolerable ranges of the calculated values, stored in the storage 52, that correspond to the factor other than the water quality, overlook and misdetection of abnormal flocculation are further prevented.

Similarly to the above, regarding the particle diameter storage 55 and the particle diameter determiner 56, the particle diameter storage 55 may store therein a plurality of tolerable particle diameter ranges of the calculated values, in correspondence with dosing rates of the coagulant and/or agitation intensities, and the particle diameter determiner 56 may acquire, from the particle diameter storage 55, one of the plurality of tolerable particle diameter ranges of the calculated values that corresponds to the dosing rate of the coagulant and/or the agitation intensity, for determination of occurrence of abnormal flocculation

INDUSTRIAL APPLICABILITY

The present disclosure provides a water treatment system that prevents overlook and misdetection of abnormal flocculation.

REFERENCE SIGNS LIST

10 To-be-treated water tank
20 Mix tank
21 Agitator
30 Flocculation tank
31 First flocculation compartment
32 Second flocculation compartment
33 Third flocculation compartment
34, 35, 36 Agitator
40 Sedimentation tank
41 Scraper
50 Fault detection device
51 Calculator
52 Storage
53 Determiner
54 Corrector
55 Particle diameter storage
56 Particle diameter determiner
57 Outputter
58 Recorder
60 Notification device
70 To-be-treated water quality measurement device
81 First floc-particle-diameter measurement device
82 Second floc-particle-diameter measurement device
90 Treated water quality measurement device
100 Water treatment system

The invention claimed is:

1. A water treatment system, comprising:
a mix tank in which water to be treated and a coagulant are mixed to obtain coagulant-mixed water;
a flocculation tank in which floc present in the coagulant-mixed water is grown;
a plurality of floc-particle-diameter measurement devices that are disposed in at least one of the mix tank and the flocculation tank and that measure particle diameters of floc in different locations at the same time along a flow direction of the coagulant-mixed water;
a fault detection device that detects abnormal floc formation by using the particle diameters of floc measured by the plurality of floc-particle-diameter measurement devices; and
a notification device that notifies occurrence of the abnormal floc formation detected by the fault detection device, wherein
the fault detection device includes: a calculator that calculates at least one of a difference and a ratio between particle diameters of floc measured by the plurality of the floc-particle-diameter measurement devices; a storage that stores therein a tolerable range of the at least one of the difference and the ratio between the particle diameters of floc; a determiner that compares a value calculated by the calculator with the tolerable range stored in the storage and that, when the calculated value is within the tolerable range, determines that normal flocculation is occurring, and when the calculated value is outside the tolerable range, determines that abnormal flocculation is occurring; and
an outputter that transmits an abnormal flocculation detection signal to the notification device when the determiner determines that abnormal flocculation is occurring.

2. The water treatment system of claim 1, wherein
the calculator calculates the ratio between the particle diameters of floc, and
the storage stores therein the tolerable range of the ratio between the particle diameters of floc.

3. The water treatment system of claim 1, further comprising:
a water quality measurement device that measures water quality of at least one of the water to be treated and the coagulant-mixed water, wherein
the storage stores therein a plurality of tolerable ranges in correspondence with the water qualities measurable by the water quality measurement device, and
the determiner compares one of the plurality of tolerable ranges that corresponds to the water quality measured by the water quality measurement device with the value calculated by the calculator.

4. The water treatment system of claim 2, further comprising:
a water quality measurement device that measures water quality of at least one of the water to be treated and the coagulant-mixed water, wherein
the storage stores therein a plurality of tolerable ranges in correspondence with the water qualities measurable by the water quality measurement device, and
the determiner compares one of the plurality of tolerable ranges that corresponds to the water quality measured by the water quality measurement device with the value calculated by the calculator.

5. The water treatment system of claim 1, further comprising:
a sedimentation tank in which floc grown in the flocculation tank is sedimented; and
a treated water quality measurement device that measures water quality of treated water obtained as a result of the sedimentation of floc in the sedimentation tank, wherein
the fault detection device further includes a corrector that corrects the tolerable range stored in the storage based on the water quality of the treated water measured by the treated water quality measurement device, and
the corrector corrects the tolerable range as needed so that it is to be determined that abnormal flocculation is occurring when treated water within a predetermined water quality range is not obtained and that it is to be determined that abnormal flocculation is not occurring when treated water within the predetermined water quality range is obtained.

6. The water treatment system of claim 2, further comprising:
a sedimentation tank in which floc grown in the flocculation tank is sedimented; and
a treated water quality measurement device that measures water quality of treated water obtained as a result of the sedimentation of floc in the sedimentation tank, wherein
the fault detection device further includes a corrector that corrects the tolerable range stored in the storage based on the water quality of the treated water measured by the treated water quality measurement device, and
the corrector corrects the tolerable range as needed so that it is to be determined that abnormal flocculation is occurring when treated water within a predetermined water quality range is not obtained and that it is to be determined that abnormal flocculation is not occurring when treated water within the predetermined water quality range is obtained.

7. The water treatment system of claim 3, further comprising:
a sedimentation tank in which floc grown in the flocculation tank is sedimented; and
a treated water quality measurement device that measures water quality of treated water obtained as a result of the sedimentation of floc in the sedimentation tank, wherein
the fault detection device further includes a corrector that corrects the tolerable range stored in the storage based on the water quality of the treated water measured by the treated water quality measurement device, and
the corrector corrects the tolerable range as needed so that it is to be determined that abnormal flocculation is occurring when treated water within a predetermined water quality range is not obtained and that it is to be determined that abnormal flocculation is not occurring when treated water within the predetermined water quality range is obtained.

8. The water treatment system of claim 4, further comprising:
a sedimentation tank in which floc grown in the flocculation tank is sedimented; and
a treated water quality measurement device that measures water quality of treated water obtained as a result of the sedimentation of floc in the sedimentation tank, wherein
the fault detection device further includes a corrector that corrects the tolerable range stored in the storage based on the water quality of the treated water measured by the treated water quality measurement device, and
the corrector corrects the tolerable range as needed so that it is to be determined that abnormal flocculation is occurring when treated water within a predetermined water quality range is not obtained and that it is to be determined that abnormal flocculation is not occurring when treated water within the predetermined water quality range is obtained.

9. The water treatment system of claim 1, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

10. The water treatment system of claim 2, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

11. The water treatment system of claim 3, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

12. The water treatment system of claim 4, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

13. The water treatment system of claim 5, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

14. The water treatment system of claim 6, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

15. The water treatment system of claim 7, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

16. The water treatment system of claim 8, further comprising:
a water quality measurement device that measures water quality of at least one of the water to be treated and the coagulant-mixed water, wherein
the fault detection device further includes: a particle diameter storage that stores therein a tolerable particle diameter range of floc in correspondence with the water quality measured by the water quality measurement device; and a particle diameter determiner that compares the particle diameter of floc measured by any of the plurality of floc-particle-diameter measurement devices with the tolerable particle diameter range stored in the particle diameter storage and that, when the particle diameter of floc is within the tolerable particle diameter range, determines that normal flocculation is occurring, and when the particle diameter of floc is beyond the tolerable particle diameter range, determines that abnormal flocculation is occurring, and
the outputter also transmits an abnormal flocculation detection signal to the notification device when the particle diameter determiner determines that abnormal flocculation is occurring.

17. The water treatment system of claim 1, wherein the plurality of floc-particle-diameter measurement devices are disposed in one of the flocculation tank, or the mix tank and the flocculation tank.

* * * * *